United States Patent [19]
Conley et al.

[11] Patent Number: 4,617,417
[45] Date of Patent: Oct. 14, 1986

[54] ALKYL 2-CARBOALKOXY-3,4-DIALKOXYBEN-ZENECARBAMATES AND PROCESS FOR THEIR PREPARATION

[75] Inventors: Richard A. Conley, Annandale; Donald L. Barton, Frenchtown, both of N.J.

[73] Assignee: Ortho Pharmaceutical Corporation, Raritan, N.J.

[21] Appl. No.: 759,975

[22] Filed: Jul. 29, 1985

[51] Int. Cl.⁴ .......................................... C07C 125/065
[52] U.S. Cl. ....................................... 560/29; 544/285
[58] Field of Search ........................... 560/29; 562/423

[56] References Cited

U.S. PATENT DOCUMENTS 3,674,882  7/1972  Houlihan .............................. 562/423

FOREIGN PATENT DOCUMENTS 0126628  11/1984  European Pat. Off. ............ 562/423

Primary Examiner—Bernard Helfin
Attorney, Agent, or Firm—Benjamin F. Lambert

[57] ABSTRACT

A process for the preparation of alkyl 2-carboxy-3,4-dialkoxybenzenecarbamates is described. The carbamates are useful intermediates in the preparation of 8-halo-5,6-dialkoxyquinazoline-2,4-diones. The diones are useful as cardiotonic agents.

12 Claims, No Drawings

ALKYL 2-CARBOALKOXY-3,4-DIALKOXYBENZENECARBAMATES AND PROCESS FOR THEIR PREPARATION

The present invention relates to a process for the preparation of alkyl 2-carboalkoxy-3,4-dialkoxybenzenecarbamates.

The 3,4-dialkoxybenzenecarbamates which are the subject of this invention have the following formula:

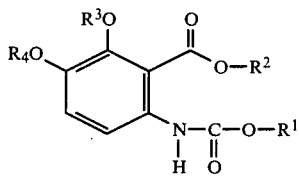

wherein $R_1$, $R_2$, $R_3$ and $R_4$ are lower alkyl having 1-5 carbon atoms.

The preparation of the 3,4-dialkoxybenzenecarbamates is illustrated by the following schematic diagram:

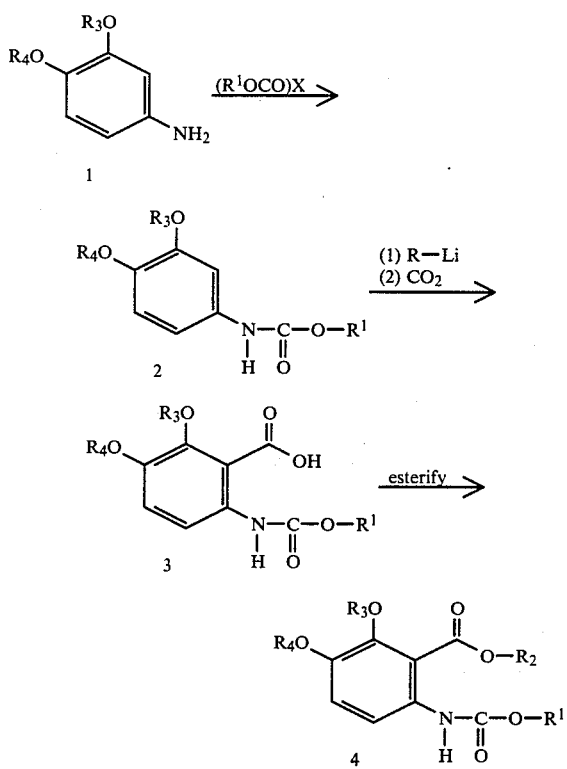

wherein $R_1$, $R_2$, $R_3$, and $R_4$ are as defined above and R is n-butyl, s-butyl or t-butyl.

In each of the steps in the process, the products are isolated where indicated and characterized by techniques known to those skilled in the art.

As can be seen by the above diagram, a 3,4-dialkoxyaniline (1) is first reacted with an alkyl haloformate such as, for example, ethyl chloroformate or methyl chloroformate, an alkyl carbonate such as, for example, ethyl carbonate or a dialkyl dicarbonate such as, for example, dibutyldicarbonate to form an alkyl 3,4-dialkoxybenzenecarbamate (2). The reaction is carried out in a suitable solvent such as, for example, chloroform, methylene chloride or tetrahydrofuran in the presence of a base such as, for example, potassium hydroxide, triethylamine, or sodium hydroxide and preferably at about room temperature. The alkyl 3,4-dialkoxybenzenecarbamate (2) is then reacted with an organolithium compound such as, for example, n-butyllithium, s-butyllithium or t-butyllithium to give the corresponding dilithium salt which is treated in situ with carbon dioxide to give the alkyl 2-carboxy-3,4-dialkoxybenzenecarbamate (3). The reaction is carried out at temperatures between about $-30°$ C. and $30°$ C. in a suitable solvent such as tetrahydrofuran or diethyl ether. The acid (3) is then esterified with an esterifying agent such as dimethylformamide dimethylacetal, a trialkylorthoformate such as, for example, triethylorthoformate, or an alcohol such as methanol, ethanol, propanol and the like with a suitable acid catalyst such as hydrochloric acid, sulfuric acid or boron trifluoride etherate to give the alkyl 2-carboalkoxy-3,4-dialkoxybenzenecarbamate (4). The reaction is carried out in a suitable solvent, however, in those instances where one or more of the reactants is a liquid, the reactants may act as a solvent for the reaction. The reaction is preferably carried out at the reflux temperature of the solvent.

The 2-carboalkoxy-3,4-dialkoxybenzenecarbamates are useful as intermediates in the preparation of 8-halo-5,6-dialkoxyquinazoline-2,4-diones such as those described in copending application Ser. No. 653,620, filed Sept. 24, 1984. The diones are useful as cardiotonic agents.

The process of this invention eliminates the regioisomer problems associated with the preparation of the quinazolinediones disclosed in U.S. Ser. No. 653,620 while shortening the overall synthesis. Some of the intermediates prepared in the synthesis of the substituted 3,4-dialkoxybenzenecarbamates are novel compounds and as such are part of the present invention.

All of the starting materials used in the process are either known materials or can be readily made from known materials by one skilled in the art.

The following examples describe the invention in greater particularity and are intended to be a way of illustrating but not limiting the invention.

EXAMPLE 1

Ethyl 3,4-dimethoxybenzenecarbamate

A solution of 919 g (6 mol) of 3,4-dimethoxyaniline in 5 L of methylene chloride was treated with 3.3 L of 2N sodium hydroxide. The reaction mixture was cooled to $12°$ C. and 603 mL (6.3 mol) of ethyl chloroformate was added at a rate to keep the temperature between $25°-30°$ C. The reaction mixture was stirred at room temperature for 2 hr and the layers were separated. The aqueous layer was extracted with $3 \times 1500$ mL of methylene chloride and the combined organic layers were dried over sodium sulfate and treated with Darco*. Evaporation gave an oil to which 3 L of ethyl acetate and 1 L of hexanes were added to crystallize the product. After cooling at $4°$ C. for 3 hr, the product was filtered and washed with $3 \times 1$ L of hexanes. Drying under vacuum gave 1133 g (84%) of the product, mp $75°-78°$ C. NMR (CDCl$_3$) $\delta$ 1.30 (t, 3H, J=7 Hz, OCH$_2$—CH$_3$), 3.83 (s, 6H, OCH$_3$), 4.18 (q, 2H, J=7 Hz, OCH$_2$—CH$_3$), 6.58 (br s, 1H, NH ), 6.70 (m, 2H, ArH), 7.12 (m, 1H, ArH).

*Activated Charcoal

EXAMPLE 2

Ethyl 2-carboxy-3,4-dimethoxybenzenecarbamate

A solution of 450 g (2 mol) of ethyl 3,4-dimethoxybenzenecarbamate in 5340 mL of tetrahydrofuran was prepared under a nitrogen atmosphere and cooled to 15° C. With cooling in an ice-water bath, 2580 mL (4 mol) of 1.56M n-butyllithium in heptane was added slowly while keeping the temperature below 30° C. Following the addition, the reaction was rapidly cooled to −10° C. and carbon dioxide was bubbled in for 1 hr. After stirring for an additional hour, the reaction was quenched with 2.5 L of 2N sodium hydroxide and the layers were separated. The aqueous layer was acidified to pH 7 with 450 mL of concentrated hydrochloric acid and extracted with 2×1.5 L of methylene chloride. The aqueous layer was then acidified to pH 2 with 400 mL of concentrated hydrochloric acid and extracted with 3×1 L of methylene chloride. The combined methylene chloride extracts (pH 2) were dried over magnesium sulfate, Darco treated, and evaporated to 247 g (46%) of the product, mp 118°–120° C. NMR (CDCl$_3$) δ 1.35 (t, 3H, J=7 Hz, OCH$_2$—C$\underline{H}_3$), 3.88 (s, 3H, OC$\underline{H}_3$), 4.07 (s, 3H, OC$\underline{H}_3$), 4.22 (q, 2H, J=7 Hz, OC$\underline{H}_2$CH$_3$), 7.13 (d, 1H, J=10 Hz, Ar$\underline{H}$), 8.20 (d, 1H, J=10 Hz, Ar$\underline{H}$), 8.75 (br s, 1H, N$\underline{H}$), 10.52 (br s, 1H, CO$_2\underline{H}$).

EXAMPLE 3

Ethyl 2-carboethoxy-3,4-dimethoxybenzenecarbamate

A solution of 10.8 g (40 mmol) of ethyl 2-carboxy-3,4-dimethoxybenzenecarbamate in 50 mL (90 mmol) of triethylorthoformate was prepared, cooled to 10° C., and 12 mL (70 mmol) of dimethylformamide diethyl acetal was slowly added. The solution was heated at reflux for 3 hr, cooled to room temperature, and evaporated to an oil. Methylene chloride (50 mL) was added and the solution was then successively extracted with 2×25 mL of 1N hydrochloric acid, 2×25 mL of 1N sodium hydroxide, and 2×25 mL of water. The organic layer was dried over sodium sulfate and evaporated to 11.8 g (90%) of the product as an oil which solidified upon standing. NMR (CDCl$_3$) δ 1.35 (m, 6H, overlapping C$\underline{H}_3$), 3.83 (s, 3H, OC$\underline{H}_3$), 3.85 (s, 3H, OC$\underline{H}_3$), 4.27 (m, 4H, overlapping C$\underline{H}_2$), 6.97 (d, 1H, J=9 Hz, Ar$\underline{H}$), 7.75 (d, 1H, J=9 Hz, Ar$\underline{H}$), 8.17 (s, 1H, N$\underline{H}$).

EXAMPLE 4

Methyl 3,4-dimethoxybenzenecarbamate

A solution of 15.3 g (0.1 mol) of 3,4-dimethoxyaniline in 60 mL of methylene chloride was treated with 55 mL of 2N sodium hydroxide. The reaction mixture was cooled to −5° C. and 7.4 mL (0.096 mol) of methyl chloroformate was added keeping the reaction temperature between 15°–25° C. The reaction was stirred 1.5 hr at 10°–20° C. and then 50 mL of water was added. The layers were separated and the aqueous layer was extracted with 4×100 mL of methylene chloride. The combined methylene chloride layers were dried over sodium sulfate and Darco treated. Evaporation gave a paste which was recrystallized from 10 mL of ethyl acetate and 10 mL of hexanes to give 18.4 g (98%) of the product, mp 83°–87° C. NMR (CDCl$_3$) δ 3.75 (s, 3H, OC$\underline{H}_3$), 3.85 (s, 3H, OC$\underline{H}_3$), 6.63 (br s, 1H, N$\underline{H}$), 6.73 (m, 2H, Ar$\underline{H}$), 7.13 (m, 1H, Ar$\underline{H}$).

EXAMPLE 5

Methyl 2-carboxy-3,4-dimethoxybenzenecarbamate

A solution of 2.11 g (0.01 mol) of methyl 3,4-dimethoxybenzenecarbamate in 25 mL of tetrahydrofuran was prepared under a nitrogen atmosphere and cooled to 0° C. With cooling, 13.4 mL (0.021 mol) of 1.57M n-butyllithium in heptane was added keeping the temperature between 15°–20° C. The reaction was then stirred at 0°–10° C. for 1.5 hr. With cooling, carbon dioxide was bubbled in for 1 hr. The resulting slurry was quenched with 15 mL of water and 25 mL of 1N sodium hydroxide. Methylene chloride (25 mL) was added and the layers were separated. The methylene chloride was then extracted with 25 mL of 1N sodium hydroxide. The combined basic aqueous layers were acidified with concentrated hydrochloric acid to pH 1–2 and then extracted with 4×25 mL of ethyl ether. The combined ether extracts were dried over sodium sulfate and evaporated to yield 1.62 g (64%) of the product as an oil. NMR (CDCl$_3$) δ 3.77 (s, 3H, OC$\underline{H}_3$), 3.90 (s, 3H, OC$\underline{H}_3$), 4.07 (s, 3H, OC$\underline{H}_3$), 7.15 (d, 1H, J=10 Hz, Ar$\underline{H}$), 7.23 (s, 1H, N$\underline{H}$), 8.13 (d, 1H, J=10 Hz, Ar$\underline{H}$), 10.88 (s, 1H, CO$_2\underline{H}$).

EXAMPLE 6

Methyl 2-carbomethoxy-3,4-dimethoxybenzenecarbamate

A solution of 1.6 g (6.3 mmol) of methyl 2-carboxy-3,4-dimethoxybenzenecarbamate in 35 mL of trimethylorthoformate and 4 mL of dimethylformamide dimethyl acetal was prepared and refluxed for 2.5 hr. The reaction mixture was evaporated and 50 mL of ethyl ether was added. The ether layer was extracted with 2×25 mL of 1N sodium hydroxide and then dried over magnesium sulfate. Evaporation gave 1.5 g (89%) of the product as a solid. NMR (CDCl$_3$) δ 3.73 (s, 3H, OC$\underline{H}_3$), 3.83 (s, 3H, OC$\underline{H}_3$), 3.87 (s, 3H, OC$\underline{H}_3$), 3.93 (s, 3H, OC$\underline{H}_3$), 6.98 (d, 1H, J=9 Hz, Ar$\underline{H}$), 7.73 (d, 1H, J=9 Hz, Ar$\underline{H}$), 9.85 (s, 1H, N$\underline{H}$).

EXAMPLE 7 t-Butyl 3,4-dimethoxybenzenecarbamate

A solution of 30.6 g (0.2 mol) of 3,4-dimethoxyaniline in 500 mL of methylene chloride was prepared. Di-tert-butyl dicarbonate (48.5 mL-0.21 mol) was added and the solution was refluxed for 4.5 hr. After cooling to room temperature, 1000 mL of methylene chloride was added and then extracted with 3×250 mL of water. The methylene chloride solution was dried over sodium sulfate, treated with Darco, and evaporated to an oil. The crude product was dissolved in 50 mL of warm isopropanol and treated with 30 g of Darco. Water (100 mL) was added and the product precipitated. After cooling in an ice water bath for 1 hr, the product was filtered and washed with 3×25 mL of water. After drying under vacuum overnight, 37.5 g (74%) of the product was obtained, mp 93°–96° C. NMR (CDCl$_3$) δ 1.50 (s, 9H, C—C$\underline{H}_3$), 3.82 (s, 3H, OC$\underline{H}_3$), 3.85 (s, 3H, OC$\underline{H}_3$), 6.48 (br s, 1H, N$\underline{H}$), 6.70 (m, 2H, Ar$\underline{H}$), 7.12 (m, 1H, Ar$\underline{H}$).

EXAMPLE 8 t-Butyl 2-carboxy-3,4-dimethoxybenzenecarbamate

A solution of 2.53 g (0.01 mol) of t-butyl 3,4-dimethoxybenzenecarbamate in 30 mL of tetrahydrofuran was prepared under a nitrogen atmosphere and cooled to −10° C. n-Butyllithium (14.2 mL of a 1.55M solution, 0.022 mol) in hexanes was added slowly keeping the temperature at 20° C. After stirring for 15 min, the reaction was cooled to −5° C. and stirred another 15 minutes. Carbon dioxide was bubbled in for 15 minutes and the reaction was then quenched with 100 mL of water. Methylene chloride (100 mL) and 50 mL of 1N sodium hydroxide were added and the layers were separated. The methylene chloride layer was extracted with another 50 mL of 1N sodium hydroxide and the combined basic aqueous layers were acidified to pH 1-2 with 10 mL of concentrated hydrochloric acid. The acidified solution was extracted with 3×100 mL of methylene chloride and the combined methylene chloride layers were dried over sodium sulfate. Evaporation gave 1.55 g (52%) of the product as an oil which solidified upon standing. NMR (CDCl$_3$) δ 1.52 (s, 9H, C—CH$_3$), 3.88 (s, 3H, OCH$_3$), 4.05 (s, 3H, OCH$_3$), 7.12 (d, 1H, J=9 Hz, ArH), 7.25 (s, 1H, NH), 8.27 (d, 1H, J=9 Hz, ArH).

EXAMPLE 9 t-Butyl 2-carbomethoxy-3,4-dimethoxybenzenecarbamate

A solution of 2.18 g (7.3 mmol) of t-butyl 2-carboxy-3,4-dimethoxybenzenecarbamate, 3 mL (22.6 mmol) of dimethylformamide dimethyl acetal, and 50 mL of trimethylorthoformate was prepared and refluxed 3 hr. The reaction mixture was evaporated to an oil which was dissolved in 150 mL of ethyl ether. The ether solution was extracted with 100 mL of saturated sodium bicarbonate solution and 100 mL of saturated sodium chloride. After drying over magnesium sulfate, evaporation gave 1.9 g (84%) of the product as an oil. NMR (CDCl$_3$) δ 1.50 (s, 9H, C—CH$_3$), 3.83 (s, 3H, OCH$_3$), 3.85 (s, 3H, OCH$_3$), 3.93 (s, 3H, OCH$_3$), 6.95 (d, 1H, J=9 Hz, ArH), 7.73 (d, 1H, J=9 Hz, ArH), 7.97 (s, 1H, NH).

Preparation of 8-chloro-5,6-dimethoxyquinazolin-2,4-dione

A. Methyl 2-carbomethoxy-6-chloro-3,4-dimethoxybenzenecarbamate

A solution of 1.35 g (5.0 mmol) of methyl 2-carbomethoxy-3,4-dimethoxybenzenecarbamate in 50 mL of chloroform was prepared and cooled to 10° C. Sulfuryl chloride (0.4 mL/5.0 mmol) was slowly added and the reaction was stirred at 10°-15° C. for 1.5 hr. The reaction was then extracted with 1×50 mL of 1N sodium hydroxide and 2×50 mL of distilled water. The chloroform solution was dried over sodium sulfate, treated with Darco, and then evaporated to 1.35 g (89%) of product as an oil which solidified upon standing. NMR (CDCl$_3$) δ 3.73 (S, 3H, OCH$_3$), 3.87 (S, 3H, OCH$_3$), 3.90 (S, 3H, OCH$_3$), 3.95 (S, 3H, OCH$_3$), 6.47 (S, 1H, NH), 7.02 (S, 1H, ArH).

B. 8-Chloro-5,6-dimethoxyquinazolin-2,4-dione

A mixture of 1.21 g (4.0 mmol) of methyl 2-carbomethoxy-6-chloro-3,4-dimethoxybenzenecarbamate and 3.17 g (20 mmol) of ammonium acetate was prepared and heated to 128° C. A solution was obtained and after one hour a white solid precipitated. The reaction mixture was cooled to room temperature, 25 mL of water was added, and the reaction mixture was cooled to 5° C. The product was filtered and washed with 2×5 mL of distilled water and 1×10 mL of methanol. Drying under vacuum gave 500 mg (49%) of white product, mp 286°–289° C. NMR (TFA) δ 4.02 (s, 3H, OCH$_3$), 4.12 (s, 3H, OCH$_3$), 7.60 (s, 1H, ArH), 9.68 (br s, 1H, NH).

What is claimed is:

1. A process for preparing a compound of the formula

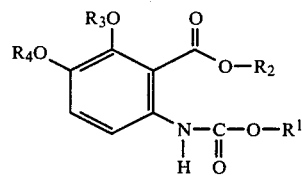

which comprises reacting a compound of the formula

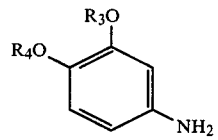

with an alkyl carbonate of the formula

R$_1$OCOR$_5$ to form a 3,4-dialkoxybenzenecarbamate of the formula

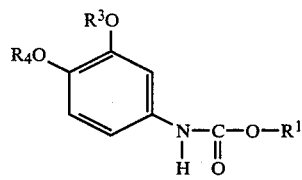

reacting the carbamate with an organolithium reagent and then reacting the product formed with carbon dioxide to form an acid of the formula

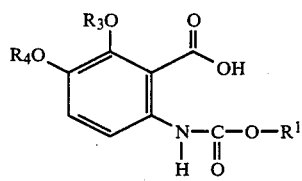

and reacting the acid with an esterifying agent, wherein R, R$_1$, R$_2$, R$_3$ and R$_4$ are lower alkyl and R$_5$ is chloro, bromo, OR or OCOOR wherein R is lower alkyl.

2. The process of claim 1 wherein the alkyl carbonate is selected from an ethyl chlorocarbonate, methyl chlorocarbonate, and di-tert-butyl dicarbonate.

3. The process of claim 1 wherein the organolithium compound is n-butyllithium.

4. The process of claim 1 wherein the esterifying agent is selected from dimethylformamide dialkylacetals, trialkylorthoformates and lower aliphatic alcohol-acid mixtures.

5. The process of claim 5 wherein the esterifying agent is trimethyl orthoformate.

6. A compound of the formula

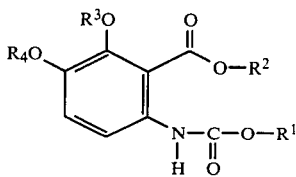

wherein $R_3$ and $R_4$ are lower alkyl; $R_1$ is straight or branched chain lower alkyl; and $R_2$ is hydrogen or lower alkyl.

7. The compound of claim 6 which is ethyl 2-carboethoxy-3,4-dimethoxybenzenecarbamate.

8. The compound of claim 6 which is methyl 2-carbomethoxy-3,4-dimethoxybenzenecarbamate.

9. The compound of claim 6 which is t-butyl 2-carbomethoxy-3,4-dimethoxybenzenecarbamate.

10. The compound of claim 6 which is t-butyl 2-carboxy-3,4-dimethoxybenzenecarbamate.

11. The compound of claim 6 which is ethyl 2-carboxy-3,4-dimethoxybenzenecarbamate.

12. The compound of claim 6 which is methyl 2-carboxy-3,4-dimethoxycarbamate.

* * * * *